(12) United States Patent
Tavori et al.

(10) Patent No.: US 9,603,568 B2
(45) Date of Patent: Mar. 28, 2017

(54) APPARATUS AND METHODS FOR CORRECTIVE GUIDANCE OF EATING BEHAVIOR AFTER WEIGHT LOSS SURGERY

(71) Applicants: Isaac Tavori, Hertzeliya (IL); Lorentz (Lior) Fleischer, Petach Tiquwa (IL)

(72) Inventors: Isaac Tavori, Hertzeliya (IL); Lorentz (Lior) Fleischer, Petach Tiquwa (IL)

( * ) Notice: Subject to any disclaimer, the term of this patent is extended or adjusted under 35 U.S.C. 154(b) by 0 days.

(21) Appl. No.: 14/736,459

(22) Filed: Jun. 11, 2015

(65) Prior Publication Data

US 2015/0325144 A1 Nov. 12, 2015

Related U.S. Application Data

(63) Continuation of application No. 12/738,079, filed as application No. PCT/IL2008/001366 on Oct. 22, 2008, now Pat. No. 9,293,062.

(60) Provisional application No. 60/980,153, filed on Oct. 15, 2007.

(51) Int. Cl.

| G09B 19/00 | (2006.01) |
|---|---|
| A61F 5/00 | (2006.01) |
| A61B 5/00 | (2006.01) |
| G06F 19/00 | (2011.01) |

(Continued)

(52) U.S. Cl.
CPC .......... *A61B 5/4866* (2013.01); *A61B 5/0086* (2013.01); *A61B 5/4238* (2013.01); *A61B 5/4836* (2013.01); *A61B 5/686* (2013.01); *A61B 8/0833* (2013.01); *A61B 8/4483* (2013.01); *A61F 5/005* (2013.01); *G06F 19/3437* (2013.01); *G09B 19/0092* (2013.01); *A61B 2562/0247* (2013.01);

(Continued)

(58) Field of Classification Search
CPC ... A61F 5/005; G06F 19/3475; G06F 19/3437
See application file for complete search history.

(56) References Cited

U.S. PATENT DOCUMENTS

| 5,724,025 A | 3/1998 | Tavori |
| 6,200,266 B1 | 3/2001 | Shokrollahi et al. |
| 8,740,768 B2 | 6/2014 | Lior et al. |

(Continued)

OTHER PUBLICATIONS

Ghosh SK et al. "Utilizing intraluminal pressure differences to predict esophageal bolus flow dynamics"; American Journal of Physiology, Gastrointestinal and Liver Physiology vol. 293; G1023-G1028, 2007.

*Primary Examiner* — Christine H Matthews
*Assistant Examiner* — Joshua D Lannu
(74) *Attorney, Agent, or Firm* — Troutman Sanders LLP

(57) ABSTRACT

Apparatuses and methods for corrective guidance of eating behavior of a patient equipped with a gastric restriction device. The apparatus provides continuous monitoring or one or more parameters related to food passing through the gastric restriction device. Each monitored parameter is processed to provide a visual indication of the current eating behavior. The visual indication is used as input to the patient or a caregiver to modify the eating behavior. In some embodiments, the apparatus includes an emergency relief mechanism that automatically relieves excess pressure developing in the gastric restriction device. In some embodiments, the apparatus is enabled to deliver an appetite suppressant to modify the eating behavior.

18 Claims, 19 Drawing Sheets

(51) Int. Cl.
*A61B 8/08* (2006.01)
*A61B 8/00* (2006.01)

(52) U.S. Cl.
CPC . *A61F 2005/002* (2013.01); *A61F 2005/0023* (2013.01); *G06F 19/3475* (2013.01)

(56) References Cited

U.S. PATENT DOCUMENTS

| | | |
|---|---|---|
| 9,293,062 B2 | 3/2016 | Tavori et al. |
| 2004/0260163 A1* | 12/2004 | Kron ................... A61B 5/205 600/345 |
| 2006/0064037 A1 | 3/2006 | Shalon et al. |
| 2006/0173238 A1* | 8/2006 | Starkebaum .......... A61F 5/0003 600/37 |
| 2006/0247719 A1 | 11/2006 | Maschino et al. |
| 2007/0156013 A1* | 7/2007 | Birk .................... A61B 5/0031 600/37 |
| 2007/0255154 A1 | 11/2007 | Lu et al. |
| 2008/0172072 A1* | 7/2008 | Pool .................... A61B 5/0084 606/151 |
| 2008/0250340 A1 | 10/2008 | Dlugos et al. |
| 2008/0250341 A1* | 10/2008 | Dlugos ............. A61B 5/02055 715/771 |
| 2009/0192415 A1 | 7/2009 | Ortiz et al. |

\* cited by examiner

APPARATUS AND METHODS FOR CORRECTIVE GUIDANCE OF EATING BEHAVIOR AFTER WEIGHT LOSS SURGERY

CROSS REFERENCE TO EXISTING APPLICATIONS

This patent application claims priority of U.S. Provisional Patent Application No. 60/980,153 filed 15 Oct. 2007, which is incorporated herein by reference in its entirety

FIELD OF THE INVENTION

The invention relates in general to systems and methods for monitoring human eating patterns and for training and modifying such patterns, in particular after weight loss surgery.

BACKGROUND OF THE INVENTION

Morbid obesity is a chronic condition. Gastric limiting techniques (e.g. "adjustable gastric banding" or AGB) are employed by surgeons to treat morbidly obese people who cannot lose weight by traditional means. In AGB, a gastric "band" made of an elastomer is placed around the stomach near its upper end. This creates a small pouch with a narrow passage into the rest of the stomach ("stoma orifice"), thus limiting the amount of food intake ("eating") by creating a feeling of fullness or uneasiness and by usually extending the time frame required to empty the pouch into the rest of the stomach. To control the size of the stoma orifice, the gastric band can be pressurized or depressurized by a physician. As a non-limiting example, the pouch is usually of a size of 50 cc to 5 cc, preferably 20 cc to 8 cc, and more preferably of about 15 cc. The stoma size can be increased or decreased with a saline solution by using a needle and syringe to access a small access port placed under the skin. The stoma orifice is governed by the amount of stomach tissue inside the band at the banding site. A desired passage size is about 12 mm in internal diameter.

The aim of restricting passage of food and liquids is to force the patient to change his/her eating behavior and thereby to induce a significant amount of weight loss. Researchers have demonstrated that the initial weight loss results after AGB are less predictable then those after gastric bypass. Patients after surgery are advised to chew their food thoroughly, eat slowly, take small bites, avoid certain foods, etc. Often, a large number of these patients do not adopt the required behavior and instead, eat forcefully, vomit, and intermittently suffer stoma occlusion events. These may result eventually in such complications as pouch enlargement, band erosion, reflux, and esophageal enlargement. In some cases, additional surgical interventions may be required.

The observation of gastric band action and the adjusting of stoma orifice by inflation/deflation are facilitated by X-ray imaging. A physician or technician acts to adjust (increase or decrease) the volume of fluid in the band based on inputs from the X-ray imaging. The volume decrease is done by removing an amount of fluid from the band via the external access port and fill line. Alternatively, components for adjusting the size of the gastric band may be implanted within the patient and, when a physical parameter such as intra-band pressure related to the patient food passage is determined, an external control unit outside the patient's body may be operated to power the implanted components to adjust the size of the band.

Monitoring the activity of the pouch created between the lower esophagus sphincter and the gastric band may generate important information related to the eating behavior of patients. Physiological parameters obtained by such monitoring may be useful to help a patient control his/her obesity, manage his/her diabetes, and monitor his/her gastro-esophageal reflux disease and the like.

Adjustable gastric restriction devices with sensors and actuators which enable control of the stoma orifice are disclosed for example in US patent applications No. 20070156013 by Birk and 20060173238 by Starkebaum. Birk discloses a self-regulating gastric band with pressure data processing, relates to a band adjustment assembly which is provided for implanting with the gastric band that includes a sensor for sensing fluid pressure in the expandable portion. The band adjustment assembly further includes a pump assembly connected to the expandable portion and to a controller that can operate the pump assembly to adjust the volume of the fluid in the band based on the sensed fluid pressure. Starkebaum's invention relates to a dynamically controlled gastric occlusion device that monitors at least one physiological parameter that varies as a function of food intake and controls the degree of gastric constriction of an occluding device, such as a gastric band, based on the monitored physiological parameter. In an embodiment, the dynamically-controlled gastric occlusion device controls the degree of gastric constriction based on time. The occluding device is dynamically opened or closed to either permit or prevent the passage of food through the gastrointestinal (GI) tract.

U.S. Pat. No. 5,724,025 to Tavori discloses a portable vital signs monitor in communication with a plurality of sensors capable of implantation, with two way communication, also allowing current diagnosis of a live body, possible reasons for abnormal diagnosis, based on physical data, anticipated behavior of the body and monitoring physical changes resulting from actual treatment.

A large number of studies have determined the following:
1) Pouch volume and stoma size are important determinants for the success of AGB.
2) Proper stoma adjustment can effect immediate and late results of the AGB and reduce complications such as Spherical Pouch Dilatation (SPD).
3) Fast eating or improper chewing of the food can lead to excessive pouch enlargement and impaired surgical results.
4) Adoption of favorable eating behavior is imperative for long term success of the AGB
5) Adoption of mal-eating behaviors can reduce the success rate of AGB.

Although gastric bands can limit food intake, it is worth recognizing that eating is a form of behavior that can be defined according to its structure (frequency duration and size of eating episodes). This pattern of behavior can be further analyzed at the level of a single meal, where the same structure (frequency duration and size of eating episodes—bites) rules and defines the meal size. In principle, this behavior operates through the skeletal musculature and is subject to conscious control. Therefore, people should be able to volitionally decide when and how to control their own eating. In practice, people find it extremely difficult to exert control and many obese people claim that their eating is out of (their) control.

AGB procedures are not known to provide a patient with visual data or information regarding his/her eating behavior pattern, yet the patient is expected to adopt different eating behavior with respect to frequency, duration or size of bite or meal. The realization and visualization of eating behavior patterns is required to the patient in order to induce conscious and correct eating behavior modification. Therefore there is a need for a tool that will provide the AGB obese patients a guided and controlled eating "pacer" that will enable them to learn and gain a new control over their eating behavior.

Out of the clinical literature from the last 15 years and over 500,000 patients with AGB it is clear that it is very difficult to obtain-hard quantitative data on the true food intake behavior of AGB obese patients. It is clear that in some AGB obese individuals, habitual food intake or its caloric value are greater than it is normally assumed to be and is often erratic and apparently unregulated. In order for health care givers to be able to advice and guide those patients to better regulate eating habits and behavior, there is clearly a need for a method and apparatus that will enable them to monitor and obtain objectively recorded eating behavior patterns. It would also be advantageous to have systems and methods to improve the action of AGB by automatically releasing excessive pressure buildups.

SUMMARY OF THE INVENTION

The invention provides, in various embodiments, devices, apparatuses and methods for gastric restriction and data collection, interpretation of eating behavior patterns and for training and eating behavior modification after weight loss surgery. In some embodiments, implanted sensors attached to a gastric band or extra corporal sensors sense, during a meal, at least one parameter like viscosity, density or quantity of a bolus (dose) of food or substance passing through the stoma, the number of boluses, the time of the passage of a bolus, intervals between boluses, duration of a meal, pressure exerted by the food bolus passage or substance and for macronutrient contents passing through the pouch and the stoma orifice produced by a restriction device. Each sensed parameter may be processed into an indication of the caloric value of the meal.

In some embodiments there is provided an apparatus and method for monitoring food passage through a gastric band stoma and for monitoring eating patterns and behavior by providing the patient real time visualization of his/her eating behavior as compared to a desired behavior. The data collected may be downloaded into a computer system that will chart the eating events and provide the patient, the surgeon/dietician information regarding the following:
Frequency of eating events during the day.
Number and size of meals.
Consistency of the consumed food (liquid, semi-liquid or solid).
Eating behavior data such as: speed of eating, quality of chewing, drinking during the meal, binge eating, night eating, vomiting.
Accurate adjustment to an "ideal stoma size".
Compliance. Eating behavior improvement.
Eating behavior adoption and assimilation.
Indication of the presence or development of a complication.
Advise patient to "stop eating" based on volume of food consumed or caloric intake.

In some embodiments, at least one sensed parameter is used to provide a command to an emergency relief valve attached to the gastric band to release pressure buildup, an action performed in prior art only manually by a physician in an emergency room.

In some embodiments, at least one sensed parameter is used to provide corrective guidance for the patient, who, with the benefit of the band's repetitive feedback capability, can adjust and change his/her eating behavior and the present perception of the body signals of hunger and satiety. This is particularly important since satiety is considered by the medical literature to be a conditioned reflex, and eating behavior is considered an acquired behavior. The patient and/or a physician or caregiver is provided with objective behavioral data regarding the patient's eating behavior. The data is used to assist the patient to adopt positive and favorable eating behaviors.

In some embodiments, at least one sensed parameter is converted into an instruction to the patient to activate an infusion pump to deliver a dose of a satiety inducing substance. The instruction generated will depend on a preset caloric level the patient is allowed to consume in that meal.

BRIEF DESCRIPTION OF THE DRAWINGS

The invention is herein described, by way of example only, with reference to the accompanying drawings, wherein.

DETAILED DESCRIPTION OF THE INVENTION

In the following description, where used, identical numbers in different figures refer to identical components.

Figure 1:
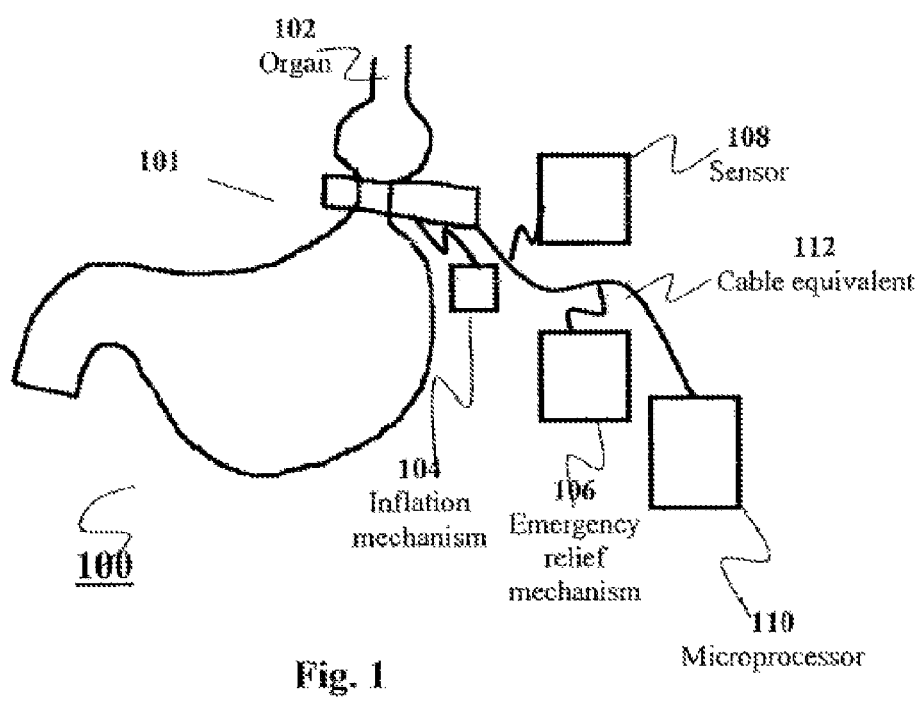
FIG. 1 shows an embodiment of an apparatus of the invention used in the stomach.

Returning now to the figures, FIG. 1 shows an embodiment of an apparatus (or "device") of the invention the form of an apparatus 100. Apparatus 100 is generally described as being implanted around an organ 102 in the alimentary, esophageal, stomach, intestine or colon tract. For ease of example, organ 102 is considered to be the stomach, apparatus 100 thereby being a gastric restriction apparatus (GRA). It is to be clearly understood that an apparatus of the invention may be implanted around other organs mentioned above, further including urinary tract or blood vessels, where its use will be based on the principles and actions described below. In common with known GRAs, apparatus 100 includes a gastric band 101, an inflation mechanism 104 operative to inflate the apparatus and bring it into intimate contact with organ 102, and at least one sensing element (sensor) 108. Inflation mechanisms useful for the purposes of the invention are known in the art, for example the balloon type vessel manufactured by Johnson & Johnson or by Allergan Corporation. Sensor 108 may be any sensor that can produce an output by sensing any physical phenomena, for example pressure, temperature, impedance, optical properties, ultrasonic properties and the like. A sensed parameter may be related to food intake in well-known ways. Such a parameter may be food viscosity, food density, food quantity, number of food boluses, bolus passage time, intervals between boluses, duration of a meal, pressure and/or macronutrient content. The description continues with reference to "a" (single) sensor, with the understanding that different sensors may be employed to provide different sensed parameters. In contrast with known GRAs, apparatus 100 further includes an emergency relief mechanism 106. Emergency relief mechanism 106 is operative to relieve the pressure inside the inflation mechanism without human intervention.

In some embodiments, apparatus 100 further includes a microcontroller (processor) 110 which communicates with sensor 108 and emergency relief mechanism 106. The communication may be two way, wired or wireless, in ways known in the art. If wired, the communication may be via a cable equivalent 112. A "cable equivalent" in this disclosure may refer to one or more electrical wires; a hydraulic vessel or a pneumatic vessel, the latter two with or without a separating membrane which separates the sensor from the inner fluid of the gastric band. A hydraulic vessel cable equivalent can be used as an ultrasound (US) emitter/reflector of intra-band events. Microcontroller 110 may be used to activate, operate or read sensor 108. The data received from the sensor may be indicative of plug flow, tissue erosion, organ dilatation and the like. Microcontroller 110 is further capable of interpreting a sensed parameter and capable of supplying inputs or commands for eating behavior modification. Data processed by microcontroller 110 may be displayed to the patient and/or to a physician, stored, or transmitted to an external entity by well-known means. In some embodiments, microcontroller 110 is capable of pacing a meal, i.e. decide on the time to start, the time to swallow and the time to end the meal.

Figure 2A:
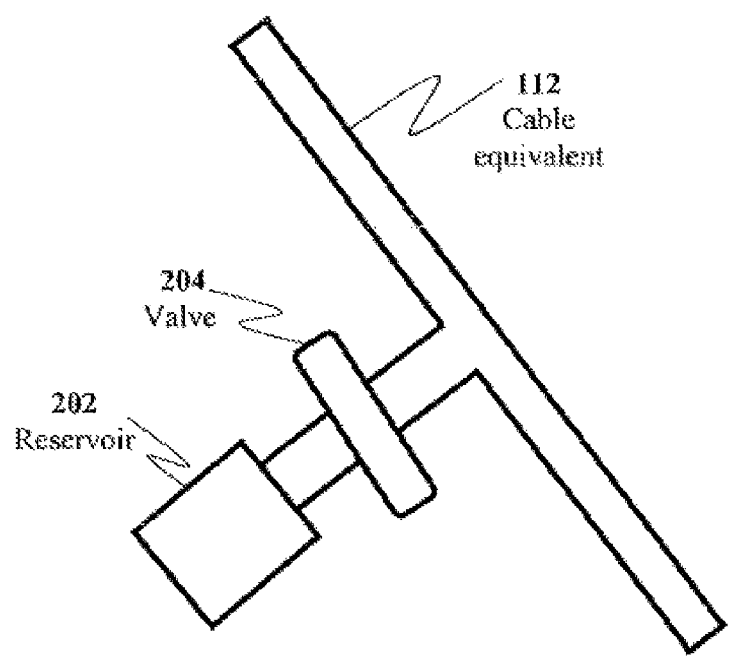
FIG. 2A shows details of one embodiment of an emergency relief mechanism.

FIG. 2A shows details of an embodiment of emergency relief mechanism in the form of a mechanism 106'. Mechanism 106' includes a reservoir 202 and a valve 204. Valve 204 couples reservoir 202 to cable equivalent 112. Reservoir 202 is dimensioned to receive a substantial portion of a calibrating saline solution, which is used to generate inflation in apparatus 100, hence relieving the stoma. Valve 204 may be a common spring loaded ball relief valve, a duckbill valve, a diaphragm valve and the like. Such valves are commonly available from Humphrey Kalamazoo, Mich. USA, operated mechanically, electromechanically or electronically, directly or by remote commands.

Figure 2B:
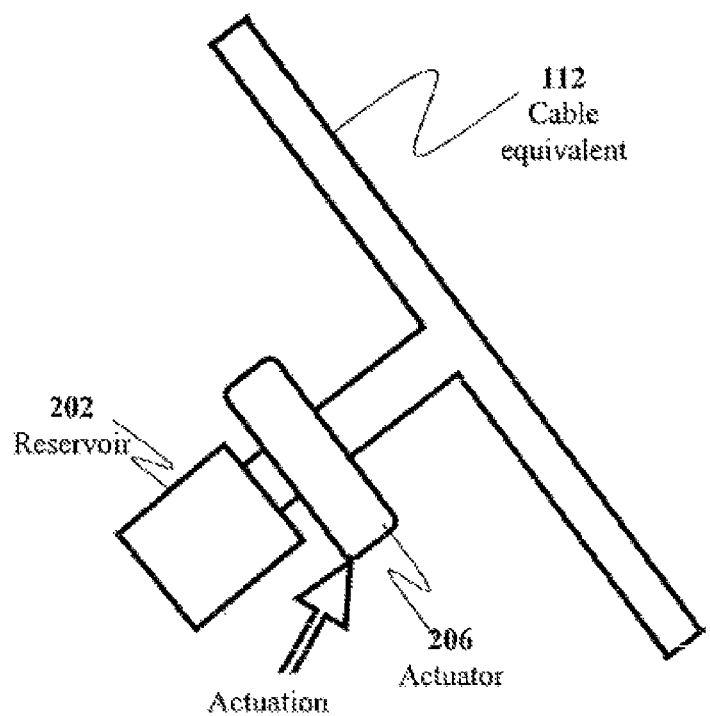
FIG. 2B shows details of another embodiment of an emergency relief mechanism.
Figure 12:
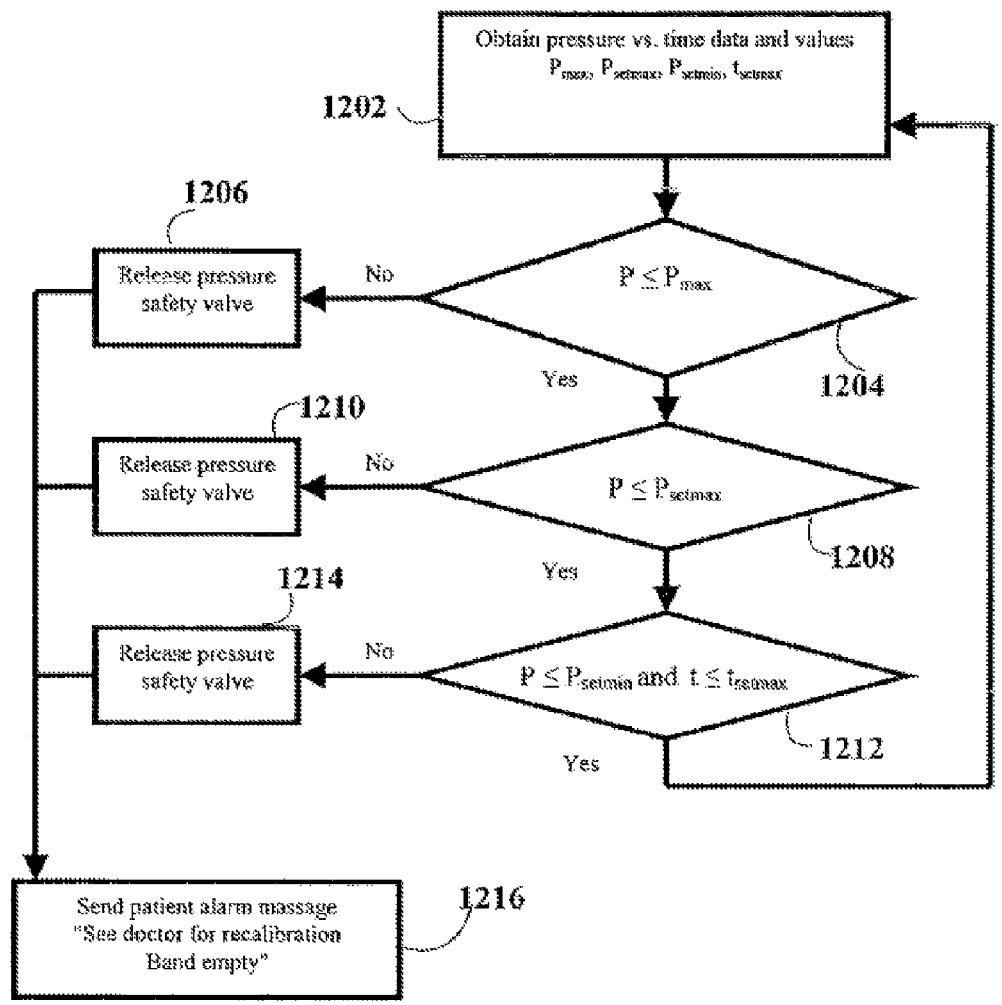
FIG. 12 describes a method of relieving pressure in the AGB using the relief emergency mechanism.

FIG. 2B shows details of another embodiment of emergency relief mechanism in the form of a mechanism 106". Mechanism 106" includes a common actuator 206 (instead of valve 204) capable of actuation and coupled to reservoir 202. Actuator 206 may be manually operated by the patient, e.g. by using extra-corporal push, magnetic, or telemetric systems, well known in the art. Another way to operate actuator 206 is by controls generated by processor 110, according to an operating algorithm described with reference to FIG. 12. Whether using valve 204 or actuator 206, when pressure reaches above a predetermined value (i.e. $P_{max}$) set in the factory, the relief valve discharges an excessive saline solution into reservoir 202. Alternatively, excessive saline may be discharged into the abdomen. In some embodiments, valve 204 and actuator 206 can be combined to work together. Sensor 108 senses both excessive pressure and pressure drop, and notifies microcontroller 110 of the pressure relief event. The patient is notified that device 100 is partially active, and is encouraged to visit a physician for monitoring and recalibration of the apparatus. The physician recalibrates device 100 using a standard procedure, empties the emergency relief mechanism by using a syringe (Huber needle) inserted in reservoir 202 and resets the emergency relief mechanism back to fully active status. The emergency relief mechanism is dimensioned such that it is visible during radiography and physically separable from a common calibration injection port or designed as an injection port.

Figure 3:
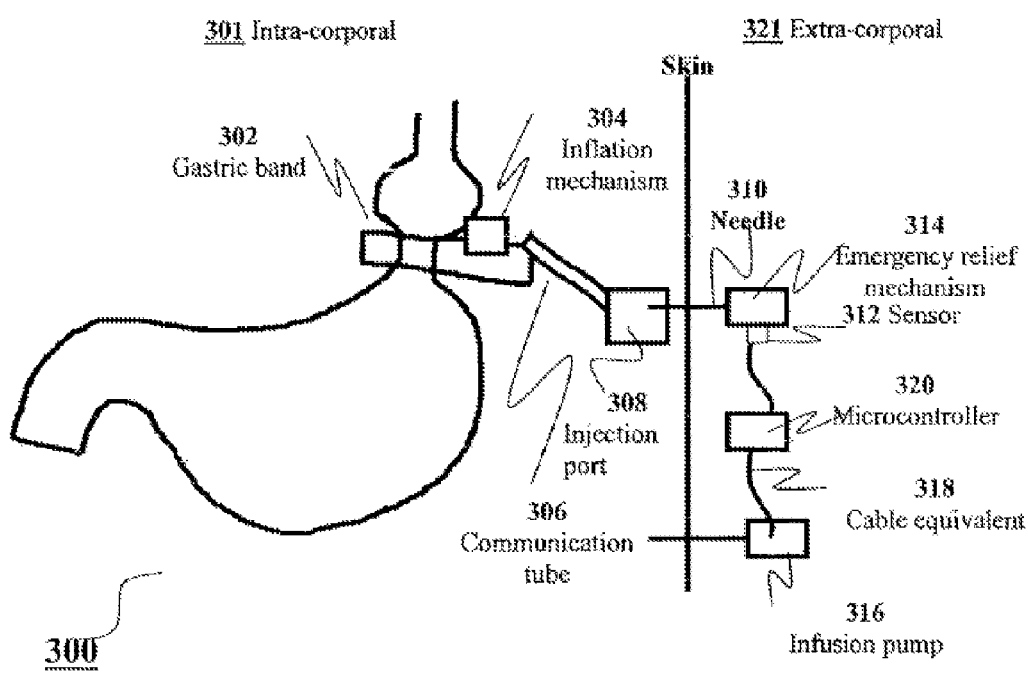
FIG. 3 shows another embodiment of an apparatus of the invention.

FIG. 3 shows an apparatus of the invention in the form of an apparatus 300.

Apparatus 300 includes an intra-corporal section 301 and an extra-corporal section 321. Intra-corporal section 301 includes a gastric band 302 with an inflation mechanism 304, a communication tube 306 and a common injection port 308. Extra-corporal section 321 includes a needle 310 used to provide access into common injection port 308 and for inflation and deflation. The needle is coupled with a sensor 312 and with an emergency relief mechanism 314. Sensor 312 and an infusion pump 316 are connected via a cable equivalent 318 to a microcontroller (processor) 320. The pump can be activated automatically or manually. In some embodiments, the pump can control intra-muscular administration of a dose of a hunger controlling hormone. An exemplary such hormone is PYY36, a well known hunger controller.

Figure 4A:
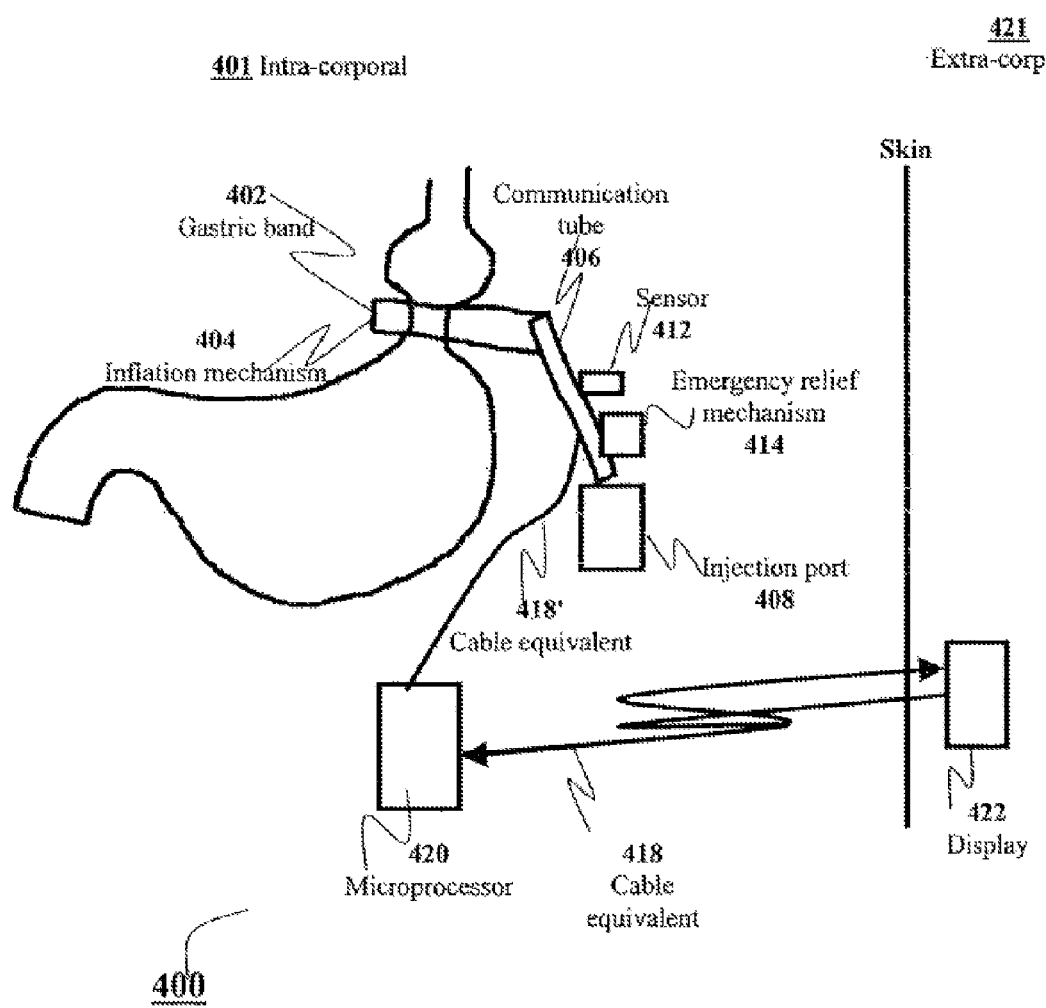
FIG. 4A shows yet another embodiment of an apparatus of the invention.

FIG. 4A shows another embodiment of an apparatus of the invention in the form of an apparatus 400. As with apparatus 300, apparatus 400 includes an intra-corporal section 401 and an extra-corporal section 421. Section 401 includes a gastric band 402 with an inflation mechanism 404, a communication tube (hydraulic line) 406 and a common injection port 408. In some embodiments, a sensor 412 and an emergency relief mechanism 414 may be connected via communication tube 406 in any position along communication tube 406. In some embodiments, sensor 412 and emergency relief mechanism 414 may be connected by a cable equivalent 418'. In some embodiments, sensor 412 and emergency relief mechanism 414 may be directly combined with gastric band 402 in a single unit. In some embodiments, sensor 412 and emergency relief mechanism 414 may be combined with a microcontroller 420 in a single unit and be in communication with gastric band 402 via a cable equivalent 418' and communication tube 406. Apparatus 400 may further include a display 422 for displaying to the patient indications related to eating behavior, eating behavior modifications and administration of substances. The displaying may be visual, tactile, auditory or sensory. Communication with microcontroller 420 is via cable equivalent 418.

Figure 4B:
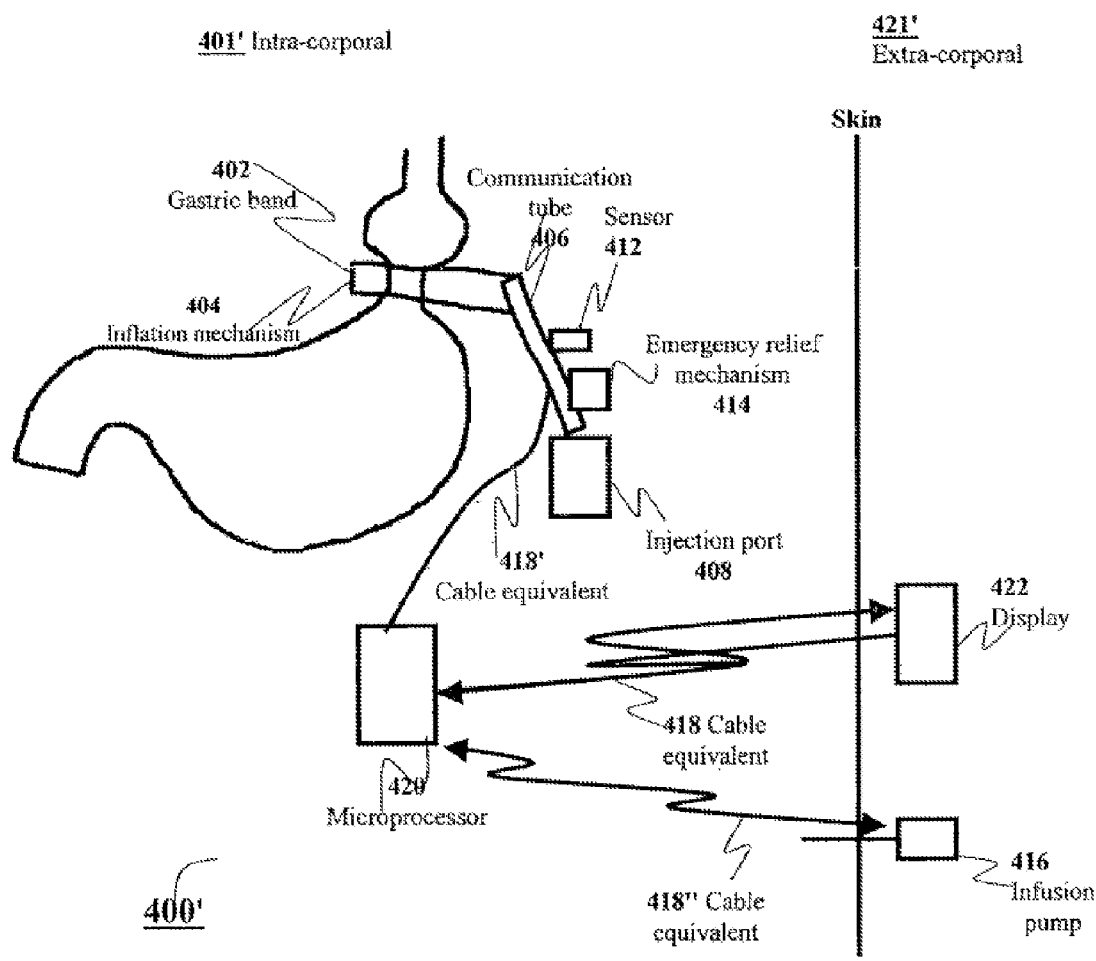
FIG. 4B shows yet another embodiment of an apparatus of the invention including infusion pump.

FIG. 4B shows another embodiment of an apparatus of the invention in the form of an apparatus 400'. As in apparatus 400, apparatus 400' includes an intra-corporal section 401' and an extra-corporal section 421'. Section 401' includes a gastric band 402 with an inflation mechanism 404, a communication tube (hydraulic line) 406 and a common injection port 408. In some embodiments of apparatus 400', a sensor 412 and an emergency relief mechanism 414 may be connected via communication tube 406 in any position along communication tube 406. In some embodiments, sensor 412 and emergency relief mechanism 414 may be connected by a cable equivalent 418'. In some embodiments, sensor 412 and emergency relief mechanism 414 may be directly combined with gastric band 402 in a single unit. In some embodiments, sensor 412 and emergency relief mechanism 414 may be combined with a microcontroller 420 in a single unit and be in communication with gastric band 402 via a cable equivalent 418' and communication tube 406. An infusion pump 416 is coupled to microprocessor 420 via a cable equivalent 418". Apparatus 400' may further include a display 422 for displaying to the patient indications related to eating behavior, eating behavior modifications and administration of substances. Display 422 and microprocessor 420 communicate via cable equivalent 418.

In some embodiments, sensors 108, 312 or 412 may be optical sensors and in particular infrared (IR) sensors.

Figure 5A:
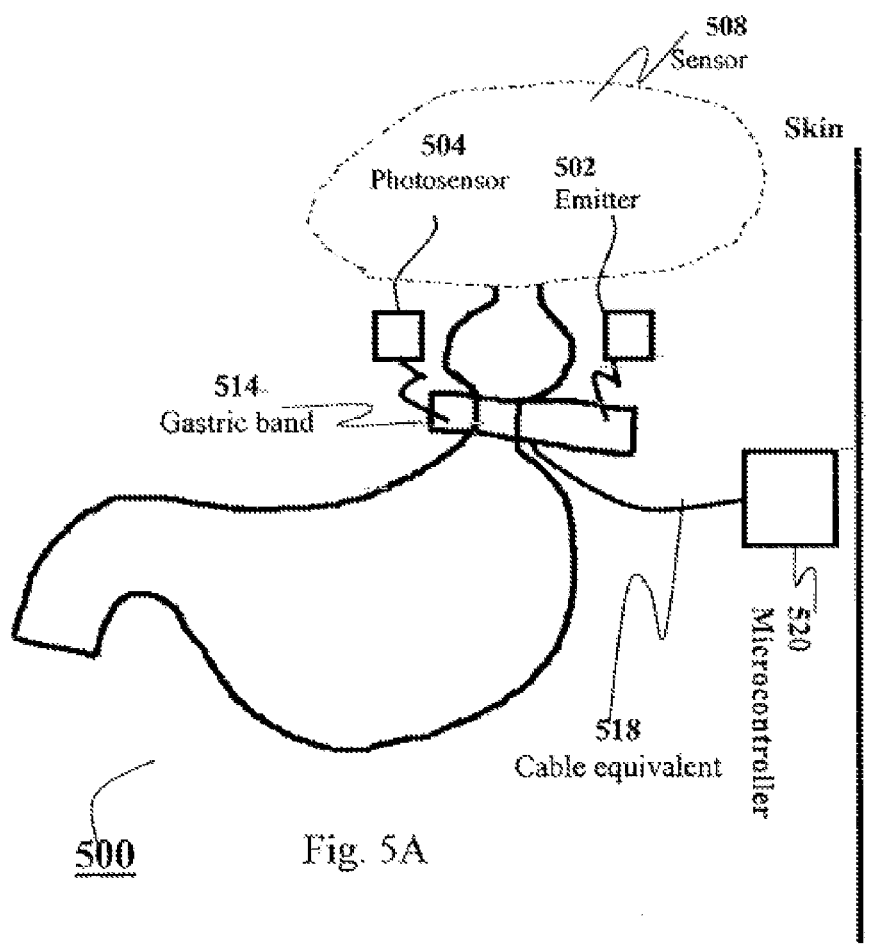
FIG. 5A describes an implanted optical sensor arrangement in an apparatus of the invention.

FIG. 5A describes an implanted optical sensor arrangement in an apparatus of the invention. An optical sensor system 508 includes an optical emitter 502 optically coupled to a photo-sensor 504. Emitter 502 and photo-sensor 504 may be positioned on opposite sides of a gastric band 514 or, optionally, may be positioned on the same side of gastric band 514. System 508 communicates with microcontroller (processor) 520 via a cable equivalent 518. In some embodiments, system 508 operates in the near infrared (NIR) spectrum range. In use, a reflective test fluid, for example a fluid that reflects infrared light, is ingested by the patient. The flow of the reflective test substance will result in IR light reflected onto photo-sensor 504, while the absence of the reflective test substance will result in little or no IR light reflected onto photo-sensor 504. Similar effects may be achieved using transmission instead of reflection. It is known that specific wavelengths and harmonies in the IR spectrum of food are directly connected to food fat, carbohydrates and protein content. In other words, an IR signal detected by the sensor can be translated by well known ways into macronutrient contents. In the embodiment above, a positive IR signal will be indicative of a flow condition, while the absence of a signal will be indicative of a no-flow condition. Sensor system 508 may be coupled to an implanted microcontroller (processor) 520, which can communicate with extra-corporal components.

Figure 5B:
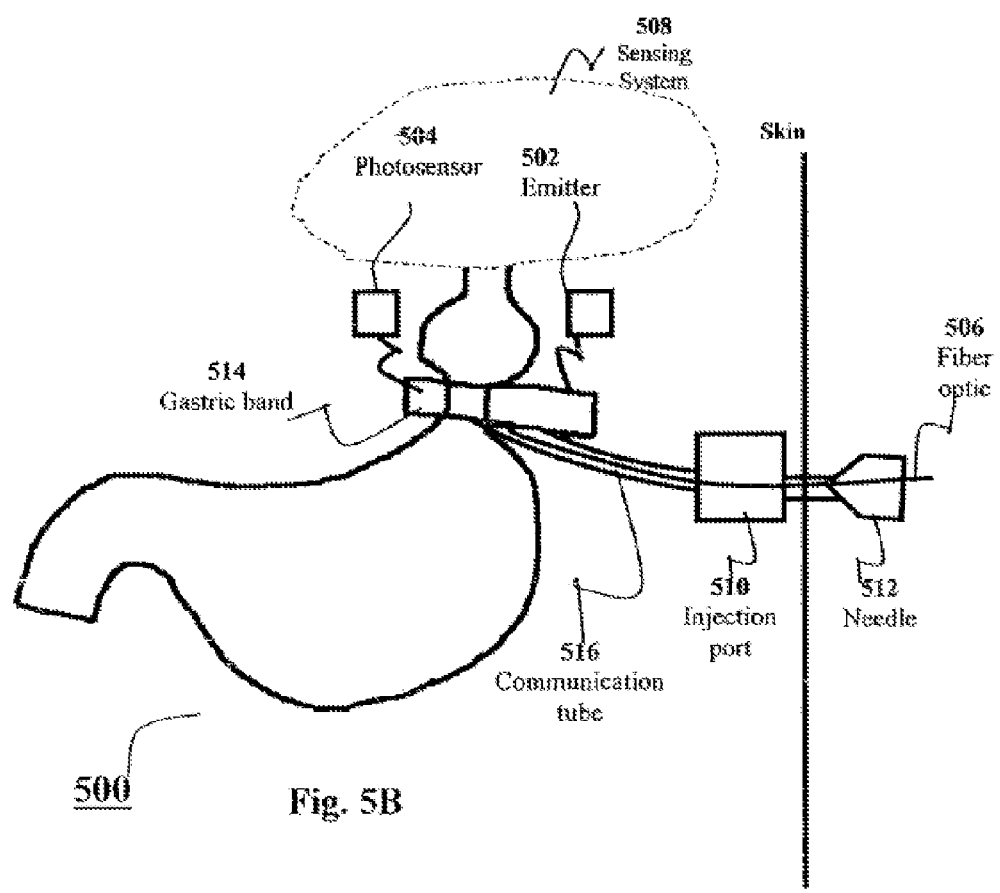
FIG. 5B shows an extra-corporeal optical sensing arrangement for an implanted apparatus of the invention.

FIG. 5B shows an extra-corporeal optical sensing arrangement for an implanted apparatus of the invention. The optical sensor system is the same as in FIG. 5A, but access to it is from external sources such as fiber optic 506, through an injection port 510, a needle 512 and a communication tube 516. The IR source and the IR sensor may be extra-corporal, with the IR light provided to gastric band 514 through suitable fiber optic means and the reflected IR light collected to the extra-corporal sensor through similarly suitable fiber optic means, as well known in the art.

It is also possible to use such arrangements with common adjustable gastric bands (AGB) known in the art.

Figure 6:
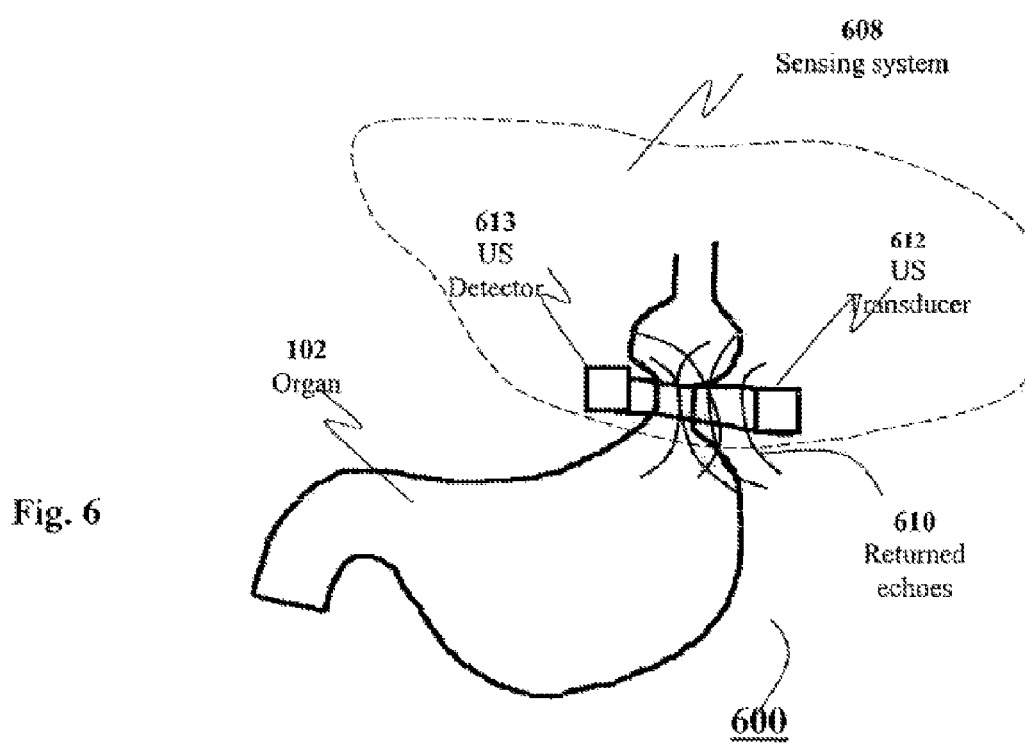
FIG. 6 shows a gastric restriction apparatus that includes an ultrasonic sensing element with an active transducer and a detector.

In some embodiments, sensors 108, 312 or 412 may be ultrasonic (US) sensors. FIG. 6 shows an apparatus 600 that includes an ultrasonic sensing element 608 with an active (electrically vibrating) US transducer 612 and a US detector 613, which are well-known in the art. Element 608 may be implanted within the inner surface of device 600 or placed immediately next to the device. The precise location of the transducer is not critical to operation, as long as the location is such that transducer 612 can effectively permit the detection of the test substance as it moves from the upper stomach pouch to the lower stomach pouch through the stoma orifice of organ 102.

Sensing element 608 may be configured to vibrate at a frequency in a range of from about 1 MHz to about 30 MHz. In some embodiments, the transducer is configured to vibrate in a range from about 5 MHz to about 15 MHz. An angle.θ is defined as the angle of incidence between the pulses and the direction of fluid flow:

$$f_D = 2 f_t V \cos \theta$$

f where $f_D$ is the Doppler frequency, $f_t$ is the vibration frequency, c is the speed of sound in tissue and V is the measured velocity of the fluid or object in motion. Solving for velocity:

$$V = f_D / (2 f_t \cos \theta)$$

Depending on the acoustic impedance of the material into which the output pulses are directed, the ultrasound output may generate return echoes 610. Return echoes are most efficiently created when there is a difference in the acoustic impedance between two regions or materials. For example, a stoma orifice without any substance will return an echo different from a stoma orifice filled with a substance. When a food substance passes through device 600, the added pressure and peristaltic motion may be measured by device 600 as a change from the stoma orifice without any substance. This change may be detected by acoustic impedance mismatch.

Figure 7:
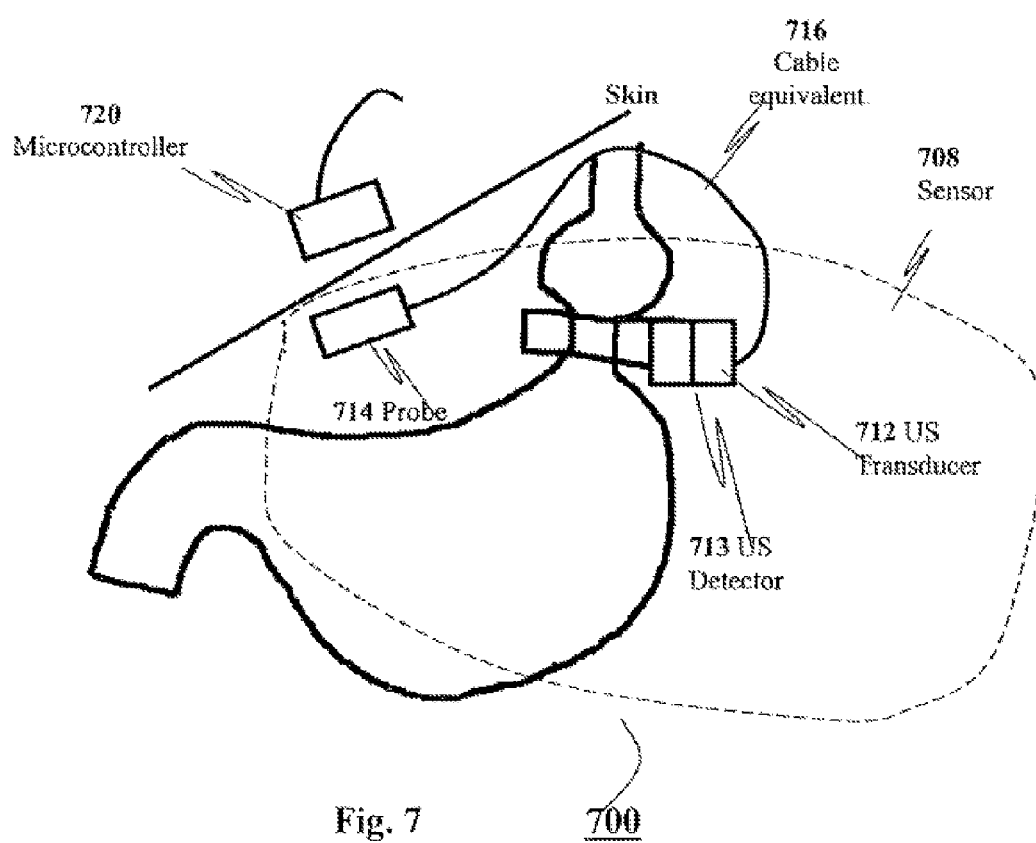
FIG. 7 shows a gastric restriction apparatus that includes a passive ultrasonic sensing element.

FIG. 7 shows an embodiment of an apparatus of the invention in the form of an apparatus 700 that includes a passive ultrasonic sensing element 708. Element 708 includes a US hydraulically vibrating transducer 712 and a US detector 713, coupled via a cable equivalent 716 to a probe 714. Element 708 is configured to be implanted in the patient, for example subcutaneously or intra-abdominally. In this configuration, the implanted device requires no active electronics to power it. Power is applied from the outside, controllable via an external microcontroller processor 720 placed on the patient's skin. A signal is generated by microcontroller processor 720. The ultrasound pulses which are created are propagated through the skin and fat to probe 714. Return echoes are transferred through cable equivalent 716 to US transducer 712 resulting in oscillations. These oscillations produce a signal which is then transferred via device 700 to US detector 713. The reflected signal mismatch between the anticipated reflection and an actual reflection is transferred to a microcontroller 720 for further analysis and display. This results in US detection of a bolus passage through the stoma.

The flow of a substance (solid or liquid food) sensed by the sensor may be described as similar to flow through a "modified" orifice plate flow meter. The present inventors have determined that in the case of a gastric band, "modified" Navier-Stokes equations may be used to describe the substance flow rate, Reynolds number, mass flow, velocity, and volumetric flow. The "modified" terminology relates to the external force component of the peristaltic motion and to the influence of stoma diameter change during food passage (flexible tube vs. rigid tube). The derivation of these equations is given next.

Derivation of Modified Navier-Stokes/Bernoulli Equations

The derivation begins with the conservation of mass, momentum, and energy being written for an arbitrary control volume. In an inertial frame of reference, the most general form of the Navier-Stokes equations can be written as:

$$\rho\left(\frac{\partial v}{\partial t} + v \cdot \nabla v\right) = -\nabla p + \nabla \cdot \mathbb{T} + f, \tag{1}$$

where V is the flow velocity, ρ is the fluid density, p is the pressure. T is the (deviatoric) stress tensor, f represents body forces (per unit volume) acting on the fluid and ∇ is the del operator. This equation is often written using the substantive derivative, making it more apparent that this is a statement of Newton's law:

$$\rho\frac{Dv}{Dt} = -\nabla p + \nabla \cdot \mathbb{T} + f. \tag{2}$$

The terms on the right side of the equation represent the body acting forces, the pressure gradient, and the forces due to the viscosity of the fluid. The body acting forces are proportional to the wetting behavior between the particles, surface and shape and the liquid part of the body of fluid. The velocity field is proportional to the pressure drop field. This field may oscillate, and create average downstream flow, intermittent flow or upstream flow. When the substance is composed of a liquid solution, flakes, flow in long constrictions with a small lumen diameter, flow separation regions, or turbulent energy losses in cases of severe stenosis, reduce the energy content of the fluid, and may also plug the flow.

In peristaltic motion, we can observe periodical pressure changes. However, opening pressure of the lower esophageal sphincter is proportional to pressure drop due to the stoma which may be created by gastric restriction device. The sum of peristaltic and other forces, generate another pressure which further facilitate movement of a substance within the lumen. Fluid or food does not typically pass through the stoma at a steady rate. Peristaltic contractions typically cause an intermittent or periodic flow rate reading in real time. The peak flow rate during this period can be an indicator of the effect of a tight restriction, predicting for example the likelihood of esophageal dilatation. In addition to the peak flow rate, the frequency or consistency of the peristaltic contractions (i.e., the number of contractions per time) can also be determined. By identifying typical patterns of test flow traces, patients can be grouped by severity of esophageal condition or by peristaltic pattern, to help determine not only how tightly their restriction should be adjusted, but also, for example, whether a more conservative diet should be selected.

The peristaltic phenomenon can be used in conjunction with the real time-flow measurement. For example, the restriction device may be tightened completely, causing complete occlusion at the stoma. The restriction device may then be slowly loosened until the desired stoma size is reached. By assessing a group of several peristaltic pulses, different degrees of stoma tightness can be more easily compared, without the need to ingest a large amount of a calibration food standard.

In order to more accurately describe flow through a gastric band, the basic Navier-Stokes equation is modified as follows $$\rho\frac{D\vec{V}}{Dt} = \rho\vec{B} - \nabla p + \mu\nabla^2 \vec{V} + \vec{F}\delta(x, y, z, \varphi, \theta, t, S) \tag{3}$$

where B represents a body force acting on a particle inside the fluid, and where the added component $\vec{F}\delta(x,y,z,\phi,\theta,t,S)$ of force per unit of shape depends on position (x,y,z), direction (θ, φ), time (t), and on a value S that represents shape. S relates to volume, surface area of the body of fluid, moment of inertia, gyration radii and other dynamic functions, generated by the travel of a fluid particle in the medium. The time (t) may be substituted with frequency (1/t). Of course, δ(x,y,z,φ,θ,t,S) may be a function, independent or dependent of any of its components Expanding formula (3) gives $$\rho\frac{\partial \vec{V}}{\partial t} + \rho\vec{V} \cdot \nabla \vec{V} = -\nabla p + \rho\vec{g} + \mu\nabla^2 \vec{V} + \vec{F}\delta(x, y, z, \varphi, \theta, t, S) \tag{4}$$

where $$\rho\frac{\partial \vec{V}}{\partial t}$$

is the local acceleration, $\rho\vec{V}\cdot\nabla\vec{V}$ is the convective acceleration, $-\nabla p$ is the pressure force per unit volume, $\rho\vec{g}$ is the body force per unit volume and $\mu\nabla^2\vec{V}$ is the viscous forces per unit volume. and $\vec{F}\delta(x,y,z,\phi,\theta,t,S)$ is an externally added component of force per unit of shape. $\vec{F}\delta(x,y,z,\phi,\theta,t,S)$ may also represent the ability of the tissue in described tract to accommodate pressure, i. e. pouch enlargement and pouch slippage.

Examination of the above equation shows that each term has units of force per unit volume, or $F/L^3$. Therefore, $\vec{F}\delta(x,y,z,\phi,\theta,t,S)$ satisfies the basic equation, since if we divide each term by a constant having those same units $(F/L^3)$ we obtain a dimensionless equation. Furthermore, the viscosity and specific gravity values also change.

Common Orifice Plate Flow Meter

In the following equations, the symbols used are as follows: $D_1$ is pouch diameter, $D_2$ is stoma diameter, $P_1$ is upstream pressure, $P_2$ is downstream pressure, ν is kinematic viscosity, μ is dynamic viscosity and ρ is upstream density. The calculation of flow rate using an orifice plate is for incompressible flow, based on the Bernoulli principle $$\frac{p_1}{\rho} + \frac{v_1^2}{2} + gz_1 = \frac{p_2}{\rho} + \frac{v_2^2}{2} + gz_2 + \frac{\Delta p_{1-2}}{\rho} \quad (5)$$

where V is the velocity of the food through the stoma, g is the gravitational constant (9.81 m/s$^2$) and z is the geodetic height. Assuming that the pressure lost is negligible (the pressure drop is obvious and included with the coefficient of discharge which is introduced below):

$$\Delta p_{1-2} = 0$$

and $$gz_1 = gz_2$$

and if velocities are substituted with flow rate $$V_1 = \frac{4Q}{\pi D_1^2}, V_2 = \frac{4Q}{\pi D_2^2} \quad (6)$$

where $V_1$ and $V_2$ are respectively the upstream and downstream velocities before and after the stoma orifice, Q is the volumetric flow rate and D is diameter. The pressure drop through the orifice because of velocity increase can be calculated as follows:

$$\frac{p_1 - p_2}{\rho} = \frac{1}{2}\left(\frac{16Q^2}{\pi^2 D_2^4} - \frac{16Q^2}{\pi^2 D_1^4}\right) \quad (7)$$

Expressing the flow rate from the previous equation leads to:

$$Q = \sqrt{\frac{1}{1 - \left(\frac{D_2}{D_1}\right)^4}} \frac{\pi D_2^2}{4} \sqrt{\frac{2(p_1 - p_2)}{\rho}} \quad (8)$$

Substituting:

$$E = \sqrt{\frac{1}{1 - \left(\frac{D_2}{D_1}\right)^4}}$$

the flow rate can be determined as:

$$Q = CeE \frac{\pi D_2^2}{4} \sqrt{\frac{2(p_1 - p_2)}{\rho}} \quad (9)$$

where C is the coefficient of discharge and e is an expansion coefficient. C can be calculated using following equation (ISO):

$$C = 0.5961 + 0.0261\beta^2 - 0.0216\beta^8 + 0.000521\left(\frac{10^6 \beta}{\text{Re}_D}\right)^{0.7} + \quad (10)$$

-continued $$\left(0.0188 + 0.0063\left(\frac{19000\beta}{\text{Re}_D}\right)^{0.8}\right)\left(\frac{10^6}{\text{Re}_D}\right)^{0.3}\beta^{3.5} +$$

$$(0.043 + 0.080e^{-10L_1} - 0.123e^{-7L_1})\left(1 - 0.11\left(\frac{19000\beta}{\text{Re}_D}\right)^{0.8}\frac{\beta^4}{1-\beta^4}\right) -$$

$$0.031\left(\frac{2L_2}{1-\beta} - 0.8\left(\frac{2L_2}{1-\beta}\right)^{1.1}\right)\beta^{1.3}$$

where $\beta$ is the diameter ratio $D_2/D_1$. $\text{Re}_D$ is the Reynolds number which can be calculated as follows:

$$\text{Re}_D = \frac{VD}{\nu} = \frac{\rho VD}{\mu} \quad (11)$$

where $\nu$ is kinematic viscosity, $\mu$ is the dynamic viscosity and $L_1$ and $L_2$ are empirical functions that relate to the particular organ through which the flow is measured. The mass flow is now given by $$G = \rho Q \quad (12)$$

and the velocities $$V_1 = \frac{4Q}{\pi D_1^2} \quad (13)$$

$$V_2 = \frac{4Q}{\pi D_2^2}$$

The abovementioned mathematical development enables obtaining measurable parameters of an instantaneous event and converting them into a "description" of food flow through the tract. This description creates meaning to volume, flow and time, which can be processed into eating behavior variables.

Figure 8:
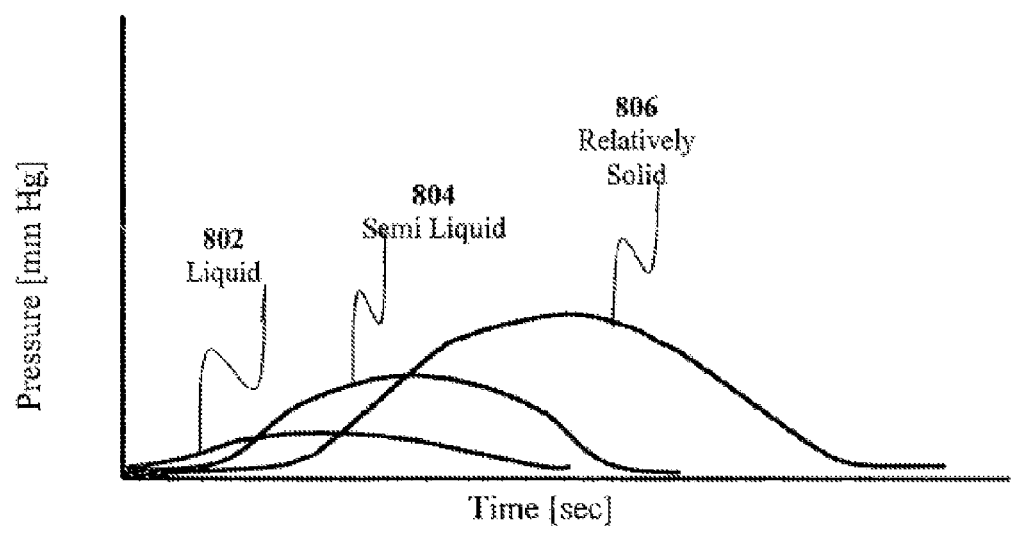
FIG. 8 shows different pressure-time curves for standard foods having different viscosities passing via the stoma orifice.

FIG. 8 shows different pressure-time curves for standard foods having different viscosities passing via the stoma orifice. The same standard foods may be ingested differently by different patients. In some cases, standard foods may be produced from regular foods and tested for viscosity using techniques such as Ford Cup. The graphs, obtained using an apparatus of the invention such as apparatus 100, show the behavior of liquids 802, semi-liquids 804 and relatively solid foods 806. The pressure-time curves show different patterns for different food viscosities. This information may be gathered into a database and displayed to the patient, among others to motivate the patient to change his/hers eating behavior.

Figure 9A:
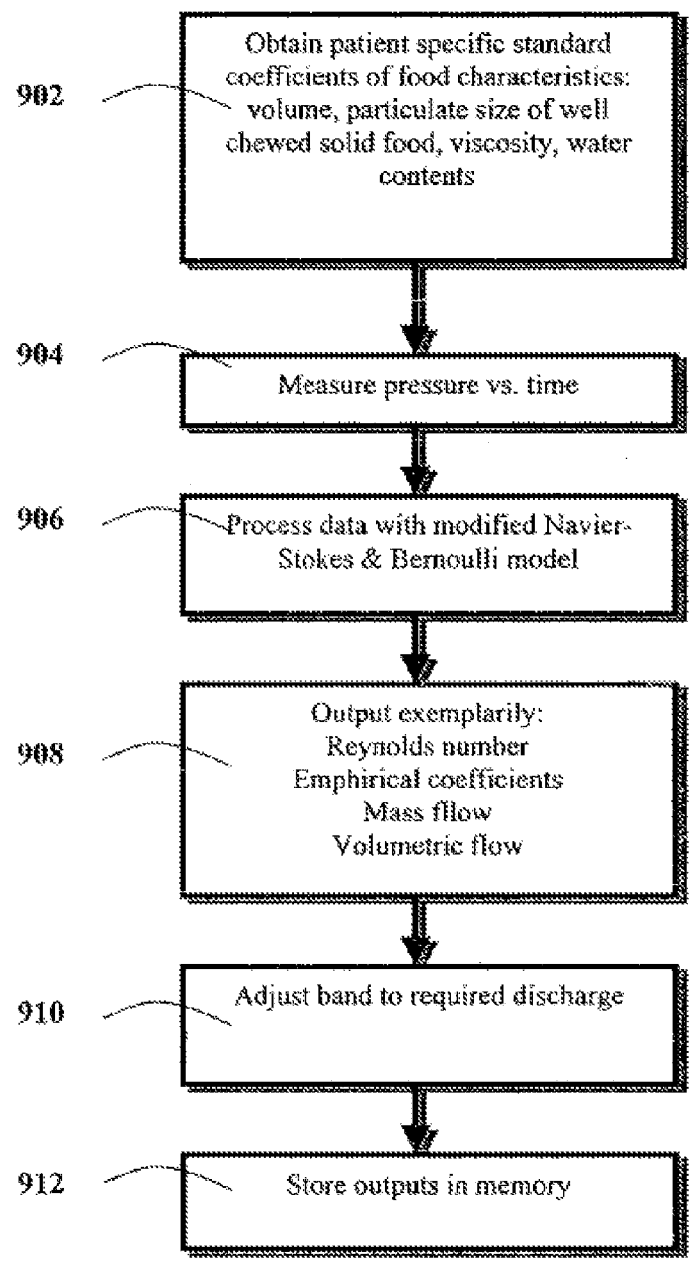
FIG. 9A describes a method for calibration of apparatus 100 based on the standard foods of FIG. 8.

FIG. 9A describes a method for calibration of apparatus 100 based on the standard foods of FIG. 8. In step 902, a patient is given a standard food with known properties. These may include viscosity, amount, division to standard bites (e.g. ranging from 2 cc to 50 cc), known particle size, water content and the like. The standard foods may be different for each patient based on individual weight loss program goals, produced from common foods and tested for viscosity. In step 904, pressure is sensed at various times and provides a pressure-time input to the system. In step 906, the pressure values are processed using the modified Navier Stokes/Bernoulli equations. The processing provides the following outputs in step 908: Reynolds number and patient specific empirical coefficients. In step 910, the outputs are used by a physician to adjust the gastric band. In step 912, the outputs (including the coefficients) are stored in a memory.

Figure 9B:
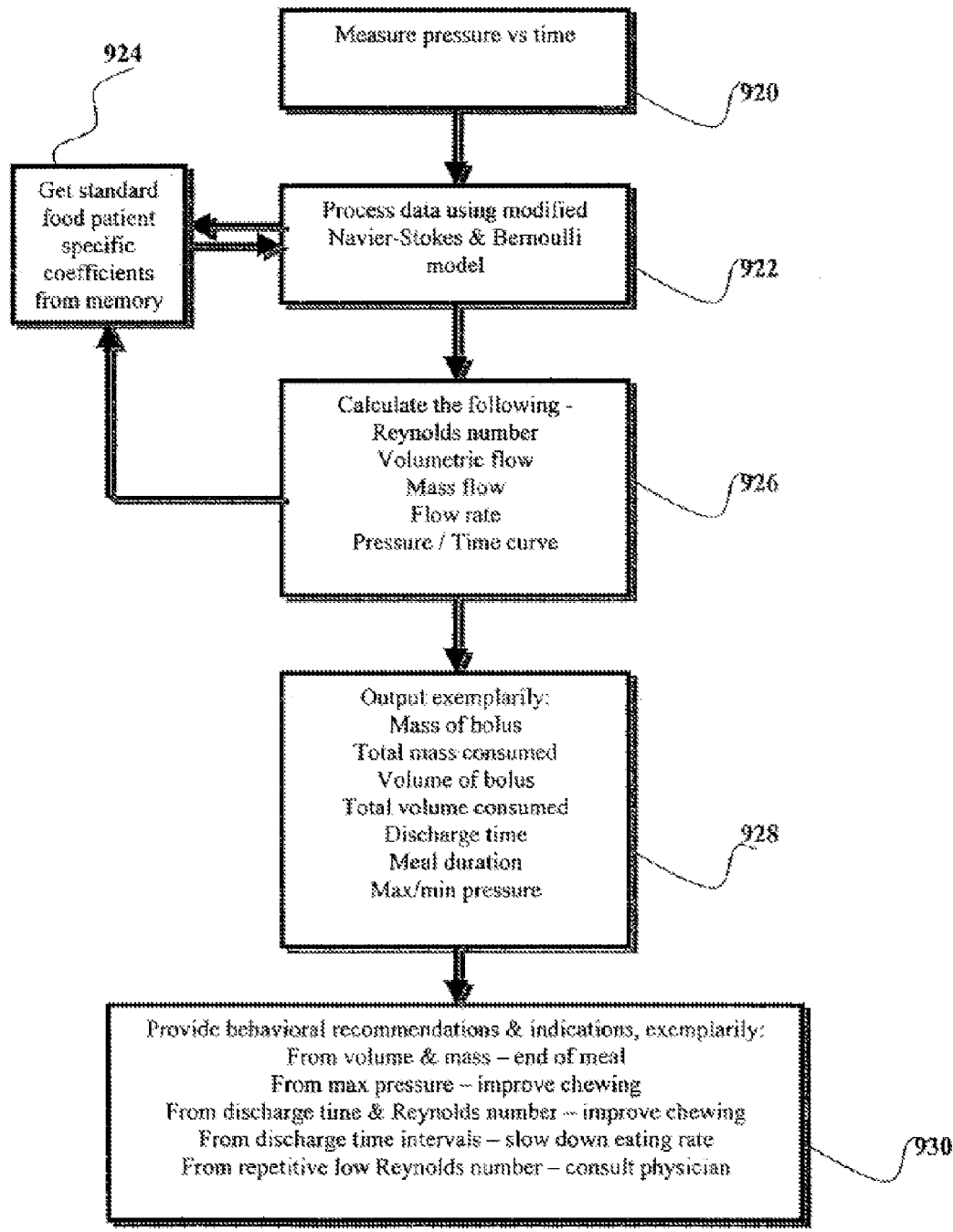
FIG. 9B describes the process of analyzing a bolus of food when the bolus passes the stoma orifice.

FIG. 9B describes the process of analyzing a bolus of food when the bolus passes the stoma orifice and relates also to the method described with reference to FIGS. 11A-11C. In step 920, pressure vs. time is measured as the food passes through the stoma orifice. In step 922, the pressure-time data is processed using the modified Navier-Stokes/Bernoulli equations. These equations are also fed standard empirical coefficients relevant to the type of food. In step 924, the data is compared to calibration values stored in memory. In step 926, processing of the data and the input of calibration values provides the following outputs: a Reynolds number, mass flow and volumetric flow, time of discharge, rate of flow and the like. Other outputs include the measured pressure vs. time. These outputs are used in step 928 to calculate "higher level data" such as bolus mass, total consumed mass, bolus volume, total consumed volume, discharge time, meal duration and maximum/minimum pressure. The higher level data is then used to provide recommendations to the patient and/or the physician or a caregiver in step 930. These recommendations may exemplarily include "next bite or wait-passage busy" (from sensed pressure) "end the meal" (from the volume and mass data), "improve chewing" (from the maximum pressure or from the discharge time and/or Reynolds number), "slow down your eating rate" (from discharge time intervals) or "consult physician" (recommendation to the patient from a repetitive low Reynolds number). When the patient follows these recommendations, eating behavior modification is provided per se.

Figure 10A:
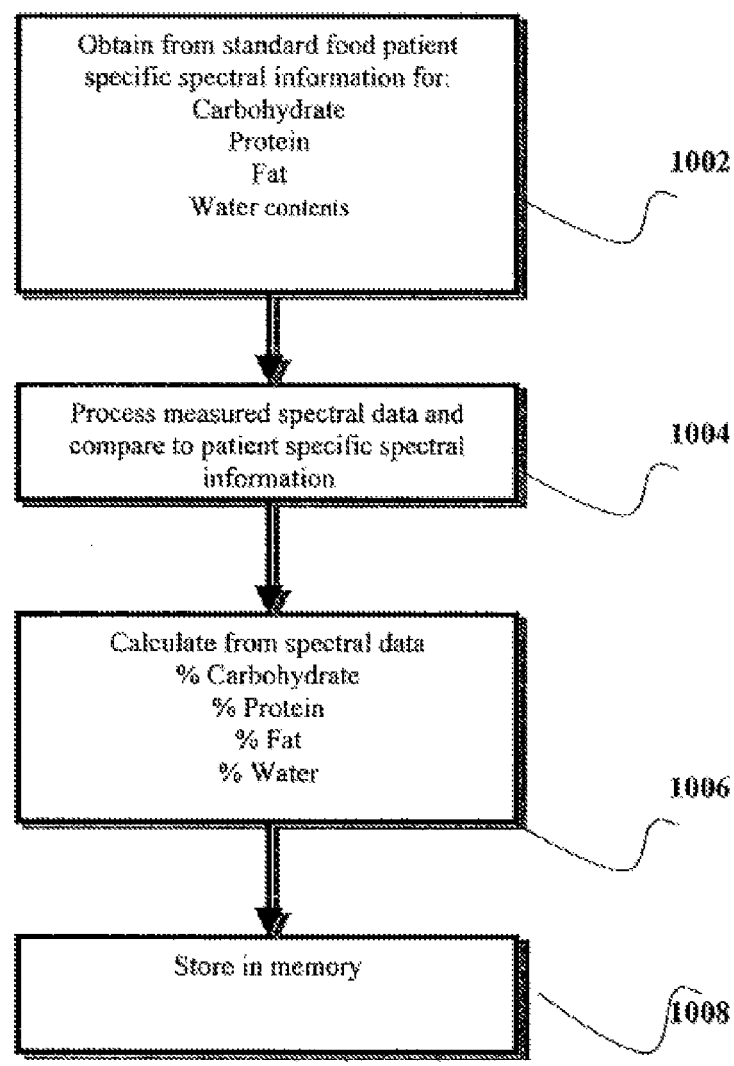
FIG. 10A describes a method for calibration of an apparatus of the invention based on standard foods caloric values using NIR technology.

FIG. 10A describes a method for calibration of an apparatus of the invention based on standard foods caloric values (known values of macronutrients) using NIR technology. As indicated in the description of FIGS. 5A and 5B, NIR provides the percentage of contents of macronutrients in a bolus. To calculate the caloric value, one needs the mass flow calculated from the modified Navier-Stokes/Bernoulli equations.

When a patient is given standard foods, different components such as fat, carbohydrates and protein absorb different wavelengths of the spectrum. In step 1002 NIR spectral data is acquired for these standard foods for each patient. In step 1004, the spectral data provides "standard" empirical coefficients related to percent of fat carbohydrates and protein for each patient. In step 1006, the percent of fat carbohydrates, protein and water is calculated from the empirical coefficients. In step 1008, the calculated percent of fat carbohydrates, protein and water for each type of standard food for each particular patient is stored in memory. Based on processed data, the physician may define a maximal caloric allowance of a meal, daily or for other periods, based on weight loss program goals for each patient.

Figure 10B:
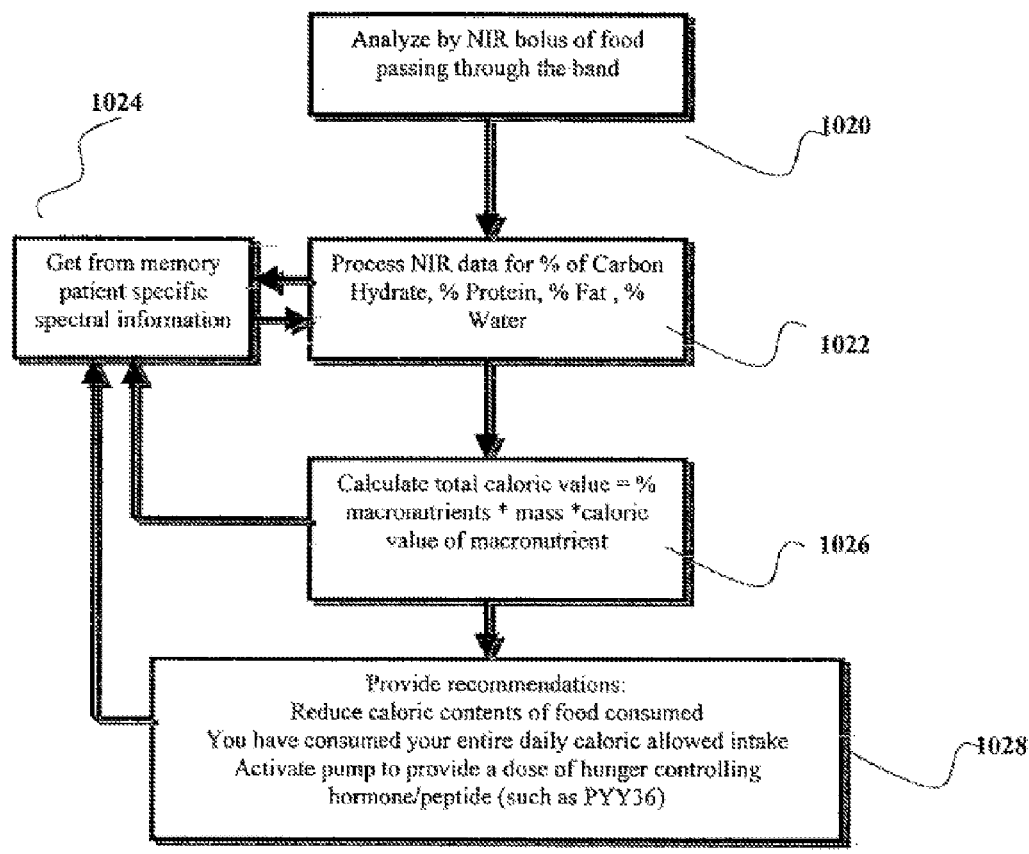
FIG. 10B describes an embodiment of a method for obtaining macronutrient contents using an apparatus of the invention with NIR technology.

FIG. 10B describes an embodiment of a method for obtaining macronutrient contents using an apparatus of the invention with NIR technology. Steps 1020 and 1022 parallel steps 1002 and 1004 in FIG. 10A. During the meal, the macronutrients contents of every bolus are calculated based on the NIR spectroscopy results, and the mass flow calculated from the modified Navier-Stokes/Bernouli equations above. The total caloric intake is calculated in step 1026. In step 1028, recommendations are provided to the patient, as described in more detail below with reference to FIGS. 11A-11C. As (or just before) the total caloric intake reaches a preset value, the system may generate an electronic signal sent by the cable equivalent to an internal or external pump that administers a preset volume of hormone or peptide such as PYY36 that controls hunger.

The following methods of use are described in detail with reference to apparatus 100, with the understanding that they may be performed with any other apparatus of the invention.

Eating Behavior Modification

In this method, apparatus 100 is used to provide inputs to a patient to change his/her eating behavior. This method takes advantage of the fact that the sensor data may be interpreted to illustrate "bad" and "good" eating patterns. The method is explained with reference to pressure as a particular sensed parameter, with the understanding that other sensed parameters obtained by NIR, ultrasound or other types of sensing may serve equally well for the stated purpose. FIGS. 11A-C show exemplary pressure-time data obtained with an apparatus of the invention.

Figure 11A:
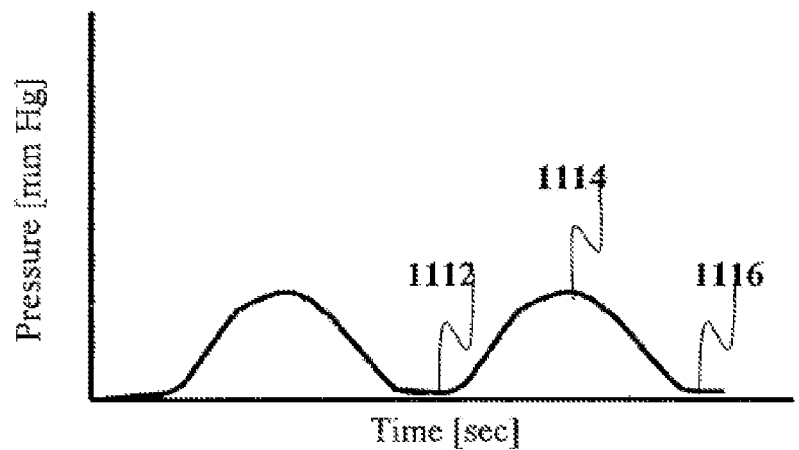
FIG. 11A describes a favorable eating behavior measured using an apparatus of the invention.

FIG. 11A describes a favorable eating behavior, exemplified by moderate pressure peaks 1114 and valleys 1112 and 1116 over time. Peak 1114 represents the presence of a bolus of food in the stoma, while valleys 1112 and 1116 represent an empty stoma orifice. This particular pressure vs. time behavior is observed when each bolus is taken only after clearing of the previous bolus from the stoma orifice. The pressure peaks are moderate, as no plug flow obstruction is present.

Figure 11B:
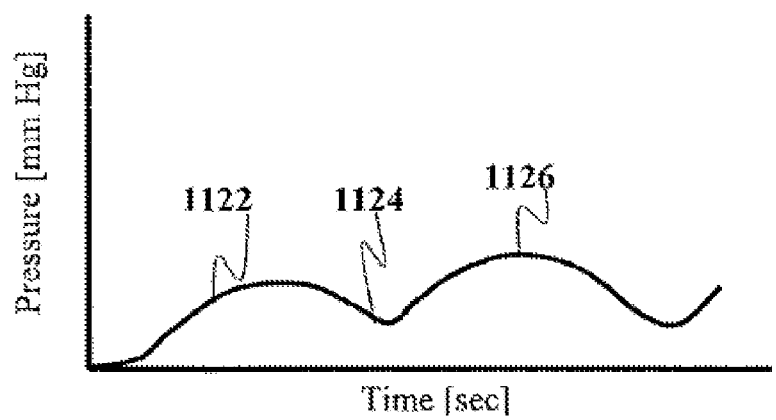
FIG. 11B describes a fast eating behavior measured using an apparatus of the invention.

FIG. 11B describes a fast eating behavior, exemplified by pressure-time pattern in which a next bolus, represented by a peak 1126, is taken before a previous bolus, represented by a peak 1122, was cleared from stoma orifice into the stomach, the clearance represented by a shallow valley 1124. As seen, valley 1124 is shallow, indicating non-complete clearing of the stoma orifice before the next bolus reaches it, i.e. representing a fast eating behavior.

Figure 11C:
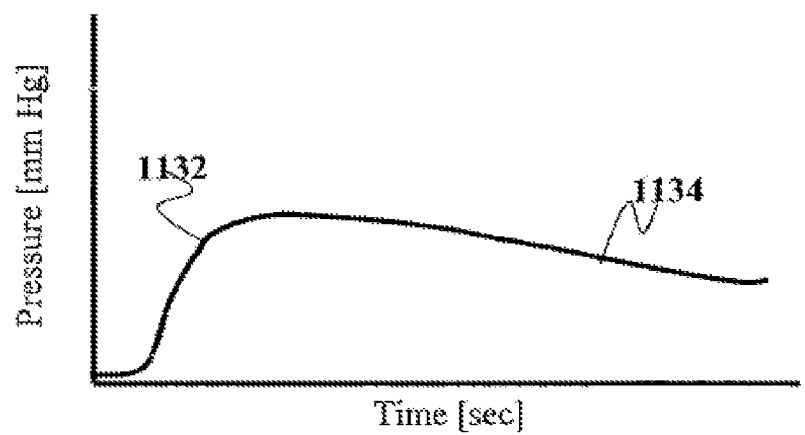
FIG. 11C describes a pattern behavior of un-chewed food measured using an apparatus of the invention.

FIG. 11C describes a pattern behavior of un-chewed food, exemplified by a pressure-time pattern that shows a larger integral under the curve. The food has high viscosity, can hardly pass the stoma orifice opening and exerts an elevated peak level of pressure 1132, creating plug flow and longer discharge time. 1134 represents the lack of a valley matching this behavior.

Assume it is desired for a patient equipped with an apparatus of the invention to change eating behavior from a "bad" one (exemplified by pressure-time curves similar to those in FIGS. 11B and 11C) to a "good" one (exemplified by the curve in FIG. 11A). The apparatus is used to acquire pressure-time curves in real time. The data in these curves is interpreted into commands to the inflation mechanism and emergency relief mechanism. The patient or the physician is presented with a graphic comparison between the pressure-time graph of the current bolus or meal and a graph of favorable behavior. The patient is then encouraged through recommendations as explained with regard to FIGS. 9B and 10B to change his/her eating behavior toward a favorable one.

After the band is properly calibrated and the basic values for the different monitored parameters are stored in the memory, it is possible to start monitoring the patient's eating behavior. For example, if the data is collected from the pressure sensor, as a pressure increase event is sensed, time recording, pressure recording, a bolus counter and the NIR sensor (when applicable) are set ON. The data collected is processed using the modified Navier-Stokes and Bernoulli equations to provide a volume description of the food flow through the gastric band. From the processed pressure-time curves, the apparatus can (by comparison of the data with stored standard constants and known values) deduce the different eating behavior conditions exemplified by FIGS.

11A-C ("good" or "bad"). As the pressure sensor senses food flowing through the band, the apparatus may provide a signal (for example a red light on the display turns ON) that the stoma orifice is "busy" and that he/she should stop eating. As the bite of food passes through the band and the pressure returns to baseline, the red light turns OFF and (for example) a second, green light turns ON, informing the patient that the food passage through the band is clear and that he/she can eat the next bite and so on. If the pattern of a bite following a bite in the manner that the passage emptying is respected as shown in FIG. 11A, the patient is provided (e.g. on the display) with a positive response regarding his speed of eating. If the pattern recorded resembles the pattern in FIG. 11B, then the patient is warned that he is eating too fast.

In terms of eating behavior interpretation, if the pressure-time curve shows that the food passing through the band had a maximal pressure equal or less than a "solid food standard" maximum pressure value, but above a "semi-liquid food" standard maximum pressure value, and if the time for the volume of food to flow through the band was in a given range, then the patient chewed the food bolus well, as shown in FIG. 11A. On the other hand, if the pressure-time data gathered show a maximum pressure higher than the standard maximum pressure value and if the food flow time took longer, then the bite of food was not chewed well, as shown in FIG. 11C. In the latter case, the patient may be given a signal in a visual, graphical, auditory, written or tactile form that the bite was not chewed enough. In case the excessive pressure exceeds certain values and/or its duration is too long, the system will open the emergency pressure relief valve and the patient will be advised through his/her personal display to visit his/her physician for band readjustment (see "Automatic gastric pressure relief" below).

In another example, when the pressure sensor senses that the present bolus still passes through the band and a second peak of pressure is sensed prior to the stoma orifice emptying, then the system will indicate to the patient that he/she is eating to fast and he/she should slow down.

To emphasize—the information provided to the patient through his/her personal display provides the patient with insight of what happens inside his/her abdomen. It paces and trains the patient to slow down the speed of eating, informs the patient about the quality of chewing and provides the patient with positive results when achieved and negative ones if not. As the patient gets visual information regarding the size of the meal, he/she can consume until personal caloric or volume limits are met. The patient can adjust the portions taken to his/her new visually induced estimates. All these changes in patient's eating behavior will assist him/her to adopt a more suitable eating behavior in response to the new physical condition created by the AGB, instead of having to do it "blindly", as done in common practice now.

Further examples of possible recommendations for the patient and indications for the health caregiver for behavior changes may include (but not be limited to) the following:
1. Pacing patient's food processing and consumption
2. Time to eat.
3. Food passage busy—stop
4. Food passage clear—go
5. Pace the food processing
6. Pace the food intake
7. Bite chewed less than required
8. No drinking during meal
9. Caloric intake too high
10. End of meal,
11. Stop eating system clogged
12. Visit your surgeon time for inspection
13. Visit your surgeon—band empty
14. Visit your surgeon—suspected problem detected For the caregiver/physician:
1) Patient eats liquid food or suspected complication
2) Patient eats too fast
3) Patients eats too much
4) Patient does not chew his food enough
5) Patient eats/drinks high caloric food/liquid
6) Patients vomits too often
7) Possible complication—erosion, band leakage, port detachment
8) Possible complication—band slippage, pouch enlargement
9) Band deflated due to occlusion
10) New calibration required Automatic Gastric Pressure Relief FIG. 12 describes a method of relieving pressure in the gastric band using the relief emergency mechanism. In step 1202, the pressure sensor provides pressure vs. time data. In step 1204, the measured pressure P is checked against a factory set maximum pressure $P_{max}$. If P is equal to or greater than $P_{max}$, the relief valve is automatically opened in step 1206, discharging excessive saline into the abdomen or into the reservoir, thereby releasing the pressure inside the AGB. This leads to a larger stoma orifice, allowing clearance of occlusion into the stoma, thus avoiding ischemia, erosion or necrotic processes in the respective organ. If the measured P is smaller than $P_{max}$, then it is in the allowed pressure zone and further processing takes place. Optionally, in step 1208, P is checked against a pressure $P_{setmax}$ set by the physician. If P is equal to or greater than $P_{setmax}$, the relief valve is automatically opened in step 1210, discharging excessive saline into the abdomen or into the reservoir, thereby releasing the pressure inside the AGB. If the measured P is smaller than $P_{setmax}$, then it is in the allowed pressure zone and further processing takes place. Further optionally, in step 1212, both P and a time of measurement t are checked against a minimal pressure set by the physician $P_{setmin}$, and a time maximum set by the physician $t_{setmax}$. If P is equal to or greater than $P_{setmin}$ or if t is equal to or greater than $t_{setmax}$, the relief valve is automatically opened in step 1214, discharging excessive saline into the abdomen or into the reservoir, thereby releasing the pressure inside the AGB. If both are smaller than the set values, then nothing is done and the measurements continue. After each pressure relief in either of steps 1206, 1210 or 1214, the patient is instructed in step 1216 to see the physician for recalibrations of the gastric band.

Controlled Delivery of a Substance

Figure 13:
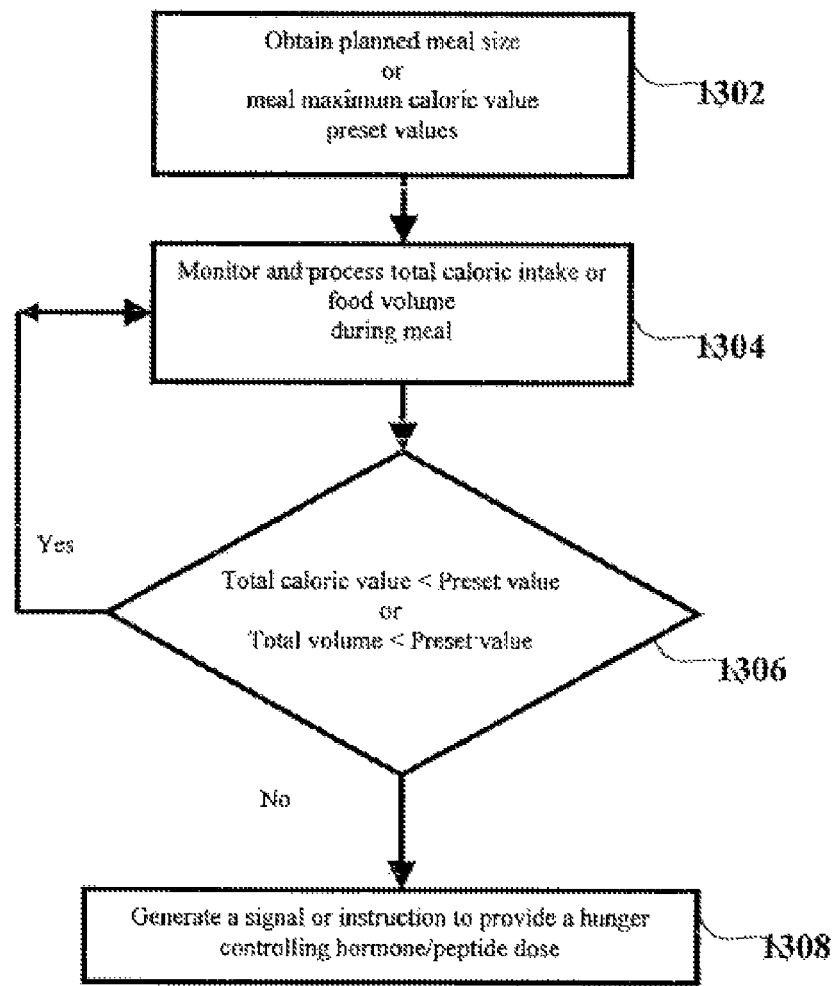
FIG. 13 describes a method of controlling automatic administration of a hunger controlling hormone or peptide.

FIG. 13 describes a method of controlling automatic administration of a hunger controlling hormone or peptide. Here, an apparatus of the invention is used to provide an input which can be converted into an instruction to the patient to activate an infusion pump to deliver a dose of the substance. The signal generation will depend on a preset caloric level the patient is allowed to consume in that meal. In step 1302, a specify meal size either by mass or by caloric values is provided as "preset" values. In step 1304, the food ingested is monitored and the total caloric intake and other parameters are obtained using any of the apparatuses of the invention. In step 1306, the total caloric intake and/or the total actual consumption volume is compared with the preset values. If either measured value exceeds the respective preset value, In case actual consumption reach to preset values, a signal is generated or an instruction is provided to an infusion pump to provide a hunger controlling hormone/ peptide such as PYY36 dose in step 1308. If the measured value does not exceed a preset value, the monitoring continues.

The various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein. In addition, citation or identification of any reference in this application shall not be construed as an admission that such reference is available as prior art to the invention.

The invention claimed is:

1. A method for modifying the eating behavior of a patient equipped with a gastric restriction apparatus (GRA), comprising steps of:
   a) monitoring, using a processor in communication with at least one sensor, at least one physical parameter directly related to food currently passing through said GRA; wherein said food currently passing through said GRA is characterized by said at least one physical parameter;
   b) analyzing, using said processor, said monitored physical parameter to provide an indication of a current eating behavior pattern;
   c) analyzing, using said processor, said indication of a current eating behavior pattern;
   d) modifying said patient's long term eating behavior by using said analysis of said indication of a current eating behavior pattern;
   wherein said at least one physical parameter is selected from a group consisting of viscosity of a bolus of said food, density of a bolus of said food, quantity of a bolus of said food, the time of passage of a bolus of said food, interval between a pair of boluses of said food, duration of a meal, and pressure applied onto said GRA by said bolus of said food; and further wherein said step of monitoring includes monitoring of flow of said food currently passing through said GRA based on at least one model selected from a group consisting of modified orifice plate flow meter model, modified Navier-Stokes equation, Bernouilli equation and any combination thereof, wherein said at least one physical parameter comprises pressure.

2. The method of claim 1, wherein said step of analyzing said monitored physical parameter further includes processing monitored pressure into an indication selected from a group consisting of volumetric flow, mass flow, analysis of eating behavior and any combination thereof.

3. The method of claim 1, wherein said step of monitoring includes monitoring intra-corporally.

4. The method of claim 1, wherein said step of monitoring includes monitoring extra-corporally.

5. The method of claim 1, wherein said step of using said indication of said current eating pattern to modify said eating behavior of said patient further comprises a step of indicating current eating behavior through a display to at least one selected from a group consisting of said patient, a caregiver, a dietician, a physician, a medical doctor, and any combination thereof.

6. The method of claim 1, wherein said step of monitoring includes ultrasonic monitoring of a stoma orifice's state and wherein said step of analyzing said monitored physical parameter includes analyzing an acoustic impedance mismatch reflective of said stoma orifice's state.

7. The method of claim 1, further comprising the step of calibrating said GRA to a desired restriction based on said at least one monitored physical parameter.

8. The method of claim 1, the method further comprising providing an emergency relief mechanism coupled to said GRA, and using said emergency relief mechanism to automatically release pressure in said GRA when an excessive pressure is indicated by said monitoring.

9. The method of claim 1, wherein the step of monitoring is preceded by a step of monitoring the same parameter on a standard food substance to obtain at least one standard food parameter and wherein a step of processing said monitored parameter includes comparing said monitored parameter to said at least one standard food parameter.

10. The method of claim 1, wherein said indication is provided to at least one selected from a group consisting of said patient, a caregiver, a dietician, a medical doctor and any combination thereof and wherein said step of using said indication is performed by at least one selected from a group consisting of said patient, a caregiver, a dietician, a medical doctor and any combination thereof.

11. The method of claim 1, wherein said indication is provided to a physician and wherein said step of using said indication is performed by at least one selected from a group consisting of said patient, a caregiver, a dietician, a medical doctor, a physician, and any combination thereof, through appropriate instructions to said patient.

12. The method of claim 1, wherein said food passing through said GRA is a member of a group consisting of solid comestibles, semi-liquid comestibles and liquid comestibles.

13. The method of claim 1, further comprising a step of identifying ingested food as a member of a group consisting of solid food, semi-liquid food, and liquid food.

14. The method of claim 1, wherein said step of analyzing said monitored physical parameter includes processing monitored pressure into Reynolds number.

15. An apparatus for data collection and interpretation of eating behavior patterns of a patient equipped with a gastric restriction apparatus (GRA) comprising:
   a) at least one sensor configured for monitoring at least one physical parameter directly related to food currently passing through said GRA; wherein said food currently passing through said GRA is characterized by said at least one physical parameter; and
   b) an intra-corporal emergency relief mechanism configured to automatically relieve pressure developing due to said food currently passing through the GRA; said intra-corporal emergency relief mechanism is set to relieve the GRA internal pressure, when pressure is above normal for eating, or when the duration of pressure is above a pre-defined time;
   wherein said at least one physical parameter is selected from the group consisting of viscosity of a bolus of said food, density of a bolus of said food, quantity of a bolus of said food, the time of passage of a bolus of said food, interval between a pair of boluses of said food, duration of a meal, pressure applied onto said GRA by said bolus of said food; and
   further wherein said monitoring includes monitoring of flow of said food currently passing through said GRA based on at least one model selected from a group consisting of modified orifice plate flow meter model, modified Navier-Stokes equation, Bernouilli equation and any combination thereof, wherein said at least one physical parameter comprises pressure.

16. The apparatus of claim 15, wherein said emergency relief mechanism includes a relief valve which is activated by a pressure input selected from a group of: provided by said at least one sensor, factory set, and physician set.

17. The apparatus of claim 15, wherein said at least one physical parameter is pressure applied onto said GRA by said bolus of said food, and wherein said at least one sensor includes a pressure sensor operative to provide pressure-time data based on a modified flow meter model.

18. The apparatus of claim 15, wherein at least one of the following is being held true (a) said at least one sensor includes an ultrasonic transducer and an ultrasonic detector (b) said food passing through said GRA is identifiable as a member of a group consisting of solid comestibles, semi-liquid comestibles and liquid comestibles; and any combination thereof.

* * * * *